United States Patent
Tian et al.

(10) Patent No.: US 9,248,089 B2
(45) Date of Patent: Feb. 2, 2016

(54) PEPTIDE-BASED COMPOUNDS AS INHIBITORS OF NEUROTRANSMITTER SECRETION

(71) Applicants: Feng Tian, Vienna, VA (US); Daniel Liang Zou, Richmond Hill (CA); Lingyun Ji, Wuhan (CN)

(72) Inventors: Feng Tian, Vienna, VA (US); Daniel Liang Zou, Richmond Hill (CA); Lingyun Ji, Wuhan (CN)

(73) Assignee: GRF (WUHAN) BIOTECHNOLOGY INC., East Lake High-Tech Development Zone, Wuhan (CN)

( * ) Notice: Subject to any disclaimer, the term of this patent is extended or adjusted under 35 U.S.C. 154(b) by 0 days.

(21) Appl. No.: 14/356,387

(22) PCT Filed: Nov. 7, 2012

(86) PCT No.: PCT/US2012/064001
§ 371 (c)(1),
(2) Date: May 5, 2014

(87) PCT Pub. No.: WO2013/070808
PCT Pub. Date: May 16, 2013

(65) Prior Publication Data
US 2014/0286885 A1    Sep. 25, 2014

Related U.S. Application Data

(60) Provisional application No. 61/556,538, filed on Nov. 7, 2011.

(51) Int. Cl.
*A61K 8/64* (2006.01)
*C07K 7/06* (2006.01)
*A61Q 19/08* (2006.01)
*A61K 38/00* (2006.01)

(52) U.S. Cl.
CPC . *A61K 8/64* (2013.01); *A61Q 19/08* (2013.01); *C07K 7/06* (2013.01); *A61K 38/00* (2013.01)

(58) Field of Classification Search
CPC ......... A61K 38/00; A61K 8/64; A61Q 19/08; C07K 7/06
See application file for complete search history.

(56) References Cited

U.S. PATENT DOCUMENTS

| | | | |
|---|---|---|---|
| 2007/0048245 A1 | 3/2007 | Belfer | |
| 2008/0108681 A1* | 5/2008 | Scimeca et al. | 514/390 |
| 2009/0068255 A1* | 3/2009 | Yu et al. | 424/450 |
| 2009/0226387 A1 | 9/2009 | Fasel et al. | |
| 2010/0021510 A1* | 1/2010 | Carreno Serraima et al. | 424/401 |
| 2010/0260823 A1* | 10/2010 | Alupei et al. | 424/445 |

FOREIGN PATENT DOCUMENTS

| | | |
|---|---|---|
| EP | 1180524 A1 | 2/2002 |
| EP | 2123673 A1 | 11/2009 |

OTHER PUBLICATIONS

Rautio Jarkko et al., Prodrugs: Design and Clinical Applications, Nature Reviews Drug Discovery, Mar. 1, 2008, 255-70, vol. 7, No. 3, Nature Publishing Group, GB.

* cited by examiner

*Primary Examiner* — Gina Justice
(74) *Attorney, Agent, or Firm* — Feng Tian (57) ABSTRACT

The present disclosure is directed to peptide-based compounds, their derivatives, pharmaceutically acceptable salts, solvates and hydrates thereof. The compounds and compositions of the present disclosure may inhibit neurotransmitter release and muscle contraction as a treatment for wrinkles. The compounds of the disclosure may be used for pathological neuronal exocytosis-mediated cosmetic and/or therapeutic purposes.

15 Claims, 3 Drawing Sheets

PEPTIDE-BASED COMPOUNDS AS INHIBITORS OF NEUROTRANSMITTER SECRETION

CROSS REFERENCE TO RELATED APPLICATION

The application is a 35 U.S.C. §371 national stage filing of International Patent Application PCT/US2012/064001 (published as WO 2013/070808 A1), filed Nov. 7, 2012, which is entitled to priority pursuant to 35 U.S.C. §119(e) to U.S. Provisional Application No. 61/556,538, filed Nov. 7, 2011. The entire disclosures of the afore-mentioned patents are hereby incorporated by reference in their entirety.

FIELD OF DISCLOSURE

The present disclosure generally relates to peptide-based compounds and, more particularly, relates to peptide-based compounds which inhibit neurotransmitter release and muscle contraction as a treatment for wrinkles.

BACKGROUND

Anti-aging products that treat wrinkling, creasing and furrowing of the skin are in high demand among consumers who want to keep their skin youthful and smooth. Treating expression lines of the face by applying topical cosmetics that are effective and non-invasive attracts the interests of both the consumer and the researcher.

Expression lines, a distinct type of wrinkle that occurs on the facial skin, are a problem for people who want to maintain a youthful appearance. The formation of expression lines is related to the facial expression muscles, whose activities during the actions of smiling, squinting, and frowning place more tension on the muscles and greater stress on the overlying skin. The facial muscle contraction is controlled by certain neurotransmitter, such as acetylcholine, the inhibition of whose release is the basis of some cosmetic products directed against expression wrinkles.

For example, *Botulinum* toxin A (BOTOX®) is one of the commonly used molecules that inhibit acetylcholine secretion and reduce facial expression wrinkles. Its mechanism hinges on the cleavage of a neuronal protein SNAP-25, whose presence is essential to the formation of a protein complex (SNARE complex) which directs and controls the release of acetylcholine accumulated in vesicles. The therapeutic and cosmetic treatment with BOTOX® is expensive, requires repeated injections, and may trigger immune reactions in patients/consumers.

U.S. Pat. No. 6,169,074 to Montal, et al. discloses combinations of peptides that interfere with the SNARE complex within the synaptic gap on the neuromuscular junction. U.S. Pat. No. 6,866,856 to Lu, et al. describes limonoids (alkaloid extracts of citrus fruits) that inhibit acetylcholine release at the neuromuscular junction of skeletal muscle. U.S. Pat. No. 7,566,464 to Belfer teaches a skin care composition that improves the appearance of expression lines of the human face comprising an extract of *Acmella oleracea* which rapidly relaxes the contractile muscle elements and suppresses the action of the expressive facial muscle based on the perceived synergy of strengthening the dermis and inhibiting the muscle tissues related to expression lines.

Furthermore, U.S. Pat. No. 7,015,192 to Blanes, et al. discovers that peptides derived from the N-terminal end of protein SNAP-25 inhibit acetylcholine release within the SNAR complex. The principle molecule, acetyl hexapeptide-3 (ARGIRELINE®) is claimed to compete with the efficacy of *Botulinum* toxin but without the risks, the injections and the high cost.

The rate and depth of skin penetration of topical cosmetics agents affects the dose of the administered agents. Peptides existing in zwitterion forms present a problem for topical applications and decrease their efficacy. Modification of the peptide structure to increase the permeability of the resulting derivatives into the target cells is one strategy to solve this problem.

Thus, there is a need in the art to discover peptide-based compounds which predominantly exist in non-charged forms when applied on the skin and inhibit neurotransmitter release and muscle contraction as a treatment for wrinkles.

SUMMARY OF THE DISCLOSURE

In accordance with one aspect of the present disclosure, there are provided compounds of Formula I

I or a pharmaceutically acceptable salt, solvate or a prodrug or a metabolite thereof, wherein $R^1$ may be $C_1$-$C_6$ alkyl; each of $R^2$ and $R^3$ may be independently H, $R^{11}$, —$CH_2OC(O)R^{12}$, or —$CH_2OC(O)OR^{13}$; each of $R^4$, $R^5$, $R^6$ and $R^7$ may be independently H, —$C(O)OR^{11}$, —$CH_2OC(O)R^{12}$, —$CH_2OC(O)OR^{11}$, or —$C(O)OCH_2OC(O)R^{12}$; $R^{11}$ is $C_2$-$C_{10}$ alkyl; $R^{12}$ may be $C_1$-$C_{10}$ alkyl; and $R^{13}$ may be $C_2$-$C_{10}$ alkyl; with the proviso that at least one of $R^4$, $R^5$, $R^6$ and $R^7$ may not be H.

In a refinement, $R^1$ of the compound of Formula I may be methyl.

In another refinement, $R^1$ of the compound of Formula I is methyl, $R^2$ and $R^3$ of the compound of Formula I may be hydrogen.

In another refinement, $R^1$ of the compound of Formula I is methyl, $R^2$ and $R^3$ of the compound of Formula I may be $R^{11}$.

In another refinement, $R^4$, $R^5$, $R^6$ and $R^7$ of the compound of Formula I may be selected from the group consisting of —$C(O)OR^{11}$, —$CH_2OC(O)R^{12}$, —$CH_2OC(O)OR^{11}$, and —$C(O)OCH_2OC(O)R^{12}$.

In another refinement, $R^4$ and $R^5$ of the compound of Formula I may be selected from the group consisting of —$C(O)OR^{11}$, —$CH_2OC(O)R^{12}$, —$CH_2OC(O)OR^{11}$, and —$C(O)OCH_2OC(O)R^{12}$.

In another refinement, $R^6$ and $R^7$ of the compound of Formula I may be selected from the group consisting of —$C(O)OR^{11}$, —$CH_2OC(O)R^{12}$, —$CH_2OC(O)OR^{11}$, and —$C(O)OCH_2OC(O)R^{12}$.

In another refinement, $R^4$ and $R^5$ of the compound of Formula I may be selected from the group consisting of —$C(O)OR^{11}$, —$CH_2OC(O)R^{12}$, —$CH_2OC(O)OR^{11}$, and —$C(O)OCH_2OC(O)R^{12}$, wherein $R^2$ and $R^3$ are hydrogen.

In another refinement, $R^4$ and $R^5$ of the compound of Formula I may be selected from the group consisting of —$C(O)OR^{11}$, —$CH_2OC(O)R^{12}$, —$CH_2OC(O)OR^{11}$, and —$C(O)OCH_2OC(O)R^{12}$, wherein $R^2$ and $R^3$ may be $R^{11}$.

In another refinement, $R^6$ and $R^7$ of the compound of Formula I may be selected from the group consisting of —$C(O)OR^{11}$, —$CH_2OC(O)R^{12}$, —$CH_2OC(O)OR^{11}$, and —$C(O)OCH_2OC(O)R^{12}$, wherein $R^2$ and $R^3$ may be hydrogen.

In still another refinement, $R^6$ and $R^7$ of the compound of Formula I may be selected from the group consisting of —$C(O)OR^{11}$, —$CH_2OC(O)R^{12}$, —$CH_2OC(O)OR^{11}$, and —$C(O)OCH_2OC(O)R^{12}$, wherein $R^2$ and $R^3$ may be $R^{11}$.

In accordance with one aspect of the present disclosure, there may be a cosmetic composition which comprises a compound of Formula I and a cosmetically acceptable adjuvant, wherein the compound is in an amount effective for the treatment of facial wrinkles or facial asymmetry In a refinement, the cosmetic composition according to claim may further comprise a safe and effective amount of at least one additional skin care actives selected from the group consisting of antioxidant, anti-inflammatory, dermal matrix precursor, skin circulation promoter, vitamin, moisturizer, and skin softener, wrinkle preventive, skin whitener, botanical dermal matrix builder, anti-cholinergic peptide, sunscreen, metalloproteinase inhibitor, and healing agent.

In another refinement, the cosmetic composition may further comprise an acceptable inert base, the acceptable inert base being selected from the group consisting of gel, lotion, cream, serum, paste, filler and transdermal patch.

In another refinement, the cosmetic composition may have the additional skin care active which may be an anti-oxidant and anti-inflammatory agent. The anti-oxidant and anti-inflammatory agent may be selected from the group comprising lycopene and green tea extract.

In another refinement, the cosmetic composition may have the additional skin care active which may be a moisturizer, anti-inflammatory and healing agent. The moisturizer, anti-inflammatory and healing agent may be selected from the group comprising allantoin.

In another refinement, the cosmetic composition may comprise the additional skin care active which may be hydrolyzed wheat protein.

In still another refinement, the cosmetic composition may comprise the additional skin care active which may be a dermal matrix collagen precursor, the dermal matrix collagen precursor being selected from a group comprising marine collagen.

In accordance with another aspect of the present disclosure, a method to prepare a compound of Formula I was disclosed. The method may comprise the steps of 1) preparing protected amino acid reagents; 2) coupling the protected amino acid reagents with a resin or a peptide attached to the resin; and 3) releasing the compound from the resin.

DETAILED DESCRIPTION OF THE DISCLOSURE

This disclosure pertains to the use of peptide-based compounds to inhibit acetylcholine release under the most favorable environment for the skin penetration. The disclosure further comprises a topical cosmetic compositions comprising a safe and effective amount of the compounds, and methods for treatment of wrinkles using the disclosed compounds and compositions.

The compounds provided by the disclosure, including solvates, stereoisomers, pharmaceutically acceptable salts, or derivatives thereof, are defined by general Formula I:

wherein
$R^1$ is $C_1$-$C_6$ alkyl;
each of $R^2$ and $R^3$ is independently H, $R^{11}$, —$CH_2OC(O)R^{12}$, or —$CH_2OC(O)OR^{13}$;
each of $R^4$, $R^5$, $R^6$ and $R^7$ is independently H, —C(O)OR$^{11}$, —$CH_2OC(O)R^{12}$, —$CH_2OC(O)OR^{11}$, or —C(O)OCH$_2$OC(O)R$^{12}$;
$R^{11}$ is $C_2$-$C_{10}$ alkyl;
$R^{12}$ is $C_1$-$C_{10}$ alkyl; and
$R^{13}$ is $C_2$-$C_{10}$ alkyl;
with the proviso that at least one of $R^4$, $R^5$, $R^6$ and $R^7$ is not H.

To facilitate the understanding of this disclosure, the meanings of some terms used in the present disclosure are included.

In this description, the abbreviations used for amino acids follow the rules of the Commission on Biochemical Nomenclature of the IUPAC-IUB specified in *Eur. J. Biochem.* 138, 9-37 (1984) and *J. Chem.* 264, 633-673 (1989).

Thus, for example, Gly represents NH$_2$—CH$_2$—C(O)OH, Gly- represents NH$_2$—CH$_2$—C(O)—, Gly represents —NH—CH$_2$—C(O)OH and -Gly- represents —NH—CH$_2$—C(O)—.

The abbreviation "Ac-" refers to the acetyl group (CH$_3$—C(O)—).

The term "acyl" refers to —C(O)R wherein R is an aryl or aliphatic group.

The term "aliphatic" refers to a hydrocarbon group that is a straight chain, a branched chain, a ring, or any combination thereof. Aliphatic groups may be saturated or unsaturated, but are not aromatic. Unsaturated aliphatic groups contain one or more double or triple bonds.

The term "alkenyl" refers to a hydrocarbon group that is a straight chain, a branched chain, a cyclic chain, or any combination thereof, with one or more carbon-carbon double bond, which is bound to the rest of the molecule by means of a single bond.

The term "alkynyl" refers to a hydrocarbon group that is a straight chain, a branched chain, a cyclic chain, or any combination thereof, with one or more carbon-carbon triple bond, which is bound to the rest of the molecule by means of a single bond.

The term "alkoxy" refers to —O—R wherein R is an alkyl group. As used within this application, $C_1$-$C_6$ alkoxy provides support for R groups that can be: a methyl group, $C_1$-$C_2$ alkyl groups, $C_1$-$C_3$ alkyl groups, $C_1$-$C_4$ alkyl groups, or $C_1$-$C_5$ alkyl groups.

The term "alkyl" refers to a saturated hydrocarbon group that is a straight chain, a branched chain, a cyclic chain, or any combination thereof. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted.

The term "aromatic" refers to a group containing at least one aromatic ring.

The term "aryl" refers to an aromatic hydrocarbon group. As used herein, unsubstituted aryl refers to an aromatic group consisting of hydrogen and carbon wherein each carbon is a ring atom. Aryl groups, as defined herein, will typically have six carbon atoms; thus, phenyl is an example of a suitable unsubstituted aryl group and ortho-tolyl is an example of a suitable substituted aryl group.

The term "Boc" is t-butyloxycarbonayl.

The term "Bu-t" is t-butyl.

The term "comprising" is meant to be open-ended, including the indicated component(s), but not excluding other elements.

The term "Fmoc" is fluorenylmethyloxycarbonyl.

The term "lower" refers to groups having between one and six atoms.

As used herein, the "additional skin care actives" refers to a safe and effective amount of at least one additional active ingredient selected from the group consisting of anti-oxidants, anti-inflammatory, dermal matrix precursors, skin circulation promoters, vitamins, moisturizers, moisture retainers, skin softeners, anti-aging and anti-wrinkle preventives, cellular renewal agents, muscle relaxing peptides, moderate to slow acting muscle relaxants and healing agents. The additional skin care actives as described herein were selected according to the criteria that they be compatible with and enhance the efficacy of the final composition.

The additional skin care actives useful herein can be categorized by the benefit they contribute and/or by their mode of action. However, the actives can in some instances provide more than one benefit or operate via more than one mode of action. Thus, the classifications herein are made for the sake of convention and are not intended to solely limit the active agent to that particular application or applications listed. (Reference for herbal constituents from Duke, J A, *CRC Handbook of Medicinal Herbs*, CRC Press, Boca Raton, Fla., 1985, 110-1); also referenced (The 5th edition (1995) of the "*International Cosmetic Ingredient Dictionary*", edited by the American industrial association CTFA) lists about 300 plants which are added as active ingredients to cosmetic agents in various formulations.

The additional skin care actives preferably include, but are not limited to: marine collagen, allantoin, hydrolyzed wheat protein, green tea extract, *Centella asiatica*, dexapanthenol or pantothenic acid, dipeptide diaminobutyroyl benzalamide diacetate, lycopene, superoxide dismutase, and hyaluronic acid. Less preferable substitutions and/or additions may be made with the following additional skins care actives: pycnogenol, vitamin K, *Juglans regia* seed extract, *Fagus sylvatica* bud extract, hibiscus flower extract, water lily extract, extract isolates of yeast, i.e. *Sacchamyces cerevisae*, and lecithin.

Within the scope of this disclosure are cosmetically and/or pharmaceutically acceptable salts of the compound of the disclosure. The term "cosmetically and/or pharmaceutically acceptable salts" includes salts customarily used to form metal salts or salts formed by adding free acids or bases. The nature of the salt is not critical, as long as it is cosmetically and/or pharmaceutically acceptable. Cosmetically and/or pharmaceutically acceptable salts of the compound of the disclosure may be obtained from acids or bases, organic or inorganic, by conventional methods which are well known to person skilled in the art, by making the appropriate acid or base react with the compound of the disclosure.

The compound of the disclosure may be used for pathological neuronal exocytosis-mediated cosmetic and/or therapeutic purposes. Among the cosmetic applications of the compound of the disclosure are the treatment and partial elimination of facial wrinkles in humans.

The disclosure provides a cosmetic composition that may include a cosmetically effective amount of at least one compound of the disclosure, along with at least one cosmetically acceptable adjuvant.

Furthermore, the disclosure provides a cosmetic composition that may comprise a cosmetically effective amount of at least one compound of the disclosure, and may further comprise a safe and effective amount of at least one additional skin care actives selected from the group consisting of antioxidant, anti-inflammatory, dermal matrix precursor, skin circulation promoter, vitamin, moisturizer, and skin softener, wrinkle preventive, skin whitener, botanical dermal matrix builder, anti-cholinergic peptide, sunscreen, metalloproteinase inhibitor, and healing agent.

Moreover, the cosmetic composition further comprises an acceptable inert base, the acceptable inert base being selected from the group consisting of gel, lotion, cream, serum, paste, filler and transdermal patch For cosmetic applications, the compound of the disclosure may be applied through any medium that produces contact between the compound and the place where the compound is to act in a mammal's body, preferably a human body.

The cosmetically effective amount of the compound that should be applied, as well as the dosage for the treatment of facial wrinkles with the compound and/or cosmetic composition of the disclosure, may depend on numerous factors. The factors may include the age and condition of the person desiring the treatment, the severity of the wrinkles, the method and frequency of the application, and the particular compound used.

The presentation of the cosmetic compositions containing the compound of the disclosure may be in any form that is suitable for application, e.g., solid, liquid or semi-solid, such as creams, ointments, gels or solutions. The application of these compositions may be by any suitable means, preferably topically, so they will include the cosmetically acceptable adjuvants necessary to make up the desired form of administration. A review of the different pharmaceutical dosage forms of the active ingredients and excipients necessary for obtaining them can be found, for example in C. Fauli i Trillo, *Tratado de Farmacia Galenica*, 1st Edition, Luzan 5 S. A. de Ediciones, Madrid (1993). Additional cosmetic preparations are described in *International Cosmetic Ingredient Dictionary and Handbook*, 13th edition, volume 4, The Personal Care Products Council (2010).

All synthetic procedures described herein can be carried out under known reaction conditions, advantageously under those described herein, either in the absence or in the presence (usually) of solvents or diluents. The solvents should be inert with respect to, and should be able to dissolve, the starting materials and other reagents used. Solvents should be able to partially or wholly solubilize the reactants in the absence or presence of catalysts, condensing agents or neutralizing agents. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

The disclosure further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the disclosure. Further, structures produced by using starting materials in the form of a reactive derivative or salt, or produced by a compound obtainable by means of the process according to the disclosure and structures resulting from processing the compounds of the disclosure in situ are also within the scope of the disclosure.

New starting materials and/or intermediates, as well as processes for the preparation thereof, are likewise the subject of this disclosure. In select embodiments, such starting materials are used and reaction conditions so selected as to obtain the desired compound(s).

Starting materials of the disclosure, are either known, commercially available, or can be synthesized in analogy to or according to methods that are known in the art. Many starting materials may be prepared according to known processes and, in particular, can be prepared using processes described in the schemes and examples. In synthesizing starting materials, functional groups in some cases are protected with suitable protecting groups when necessary.

Methods involving the use of protecting groups may be used. Particularly, if one or more functional groups, for example carboxy, hydroxy, amino, or mercapto groups, are or need to be protected in preparing the compounds of the disclosure, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. The person skilled in the art knows, or can easily establish, which protecting groups are suitable with the reactions described herein.

The protection of functional groups by protecting groups, the protecting groups themselves, and their removal reactions (commonly referred to as "deprotection") are described, for example, in standard reference works, such as J. F. W. McOmie, *Protective Groups in Organic Chemistry*, Plenum Press, London and New York (1973); T. W. Greene and P. G. M. Wuts, *Protective Groups in Organic Synthesis*, 3rd edition, John Wiley and Sons (1999); E. Gross and J. Meienhofer *The Peptides*, Volume 3, Academic Press, London and New York (1981); H. Weyl, *Methoden der Organischen Chemie* (*Methods of Organic Chemistry*), 4th edition, Volume 15/1, Georg Thieme Verlag, Stuttgart (1974); H.-D. Jakubke and H. Jescheit, Aminosäuren, *Peptide, Proteine* (*Amino Acids, Peptides, Proteins*), Verlag Chemie, Weinheim, Deerfield Beach, and Basel (1982); and in Jochen Lehmann, *Chemie der Kohlenhydrate: Monosaccharide and Derivate* (*Chemistry of Carbohydrates: Monosaccharides and Derivatives*), Georg Thieme Verlag, Stuttgart (1974).

Additional methods of synthesizing compounds of Formula I and their synthetic precursors, including those within routes not explicitly shown herein, are within the means of chemists of ordinary skill in the art. The methods described herein may also additionally include steps, either before or after the steps described specifically herein, to add or remove suitable protecting groups in order to ultimately allow synthesis of the compounds herein. Synthetic chemistry transformations useful in synthesizing the inhibitor compounds described herein are known in the art and include, for example, those such as described in R. Larock, *Comprehensive Organic Transformations*, VCH Publishers (1989); L. Fieser and M. Fieser, *Fieser and Fieser's Reagents for Organic Synthesis*, John Wiley and Sons (1994); A. Katritzky and A. Pozharski, *Handbook of Heterocyclic Chemistry*, 2nd edition (2001) and L. Paquette, editor, *Encyclopedia of Reagents for Organic Synthesis*, John Wiley and Sons (1995) and subsequent editions thereof.

The compounds of the disclosure may be prepared by a number of processes as generally described below and more specifically in the example hereinafter.

The compound of the disclosure can be synthesized through conventional methods for solid phase chemical peptide synthesis using Fmoc and/or Boc-based synthetic methodology on Rink-amide resins with modifications obvious to person skilled in the art. Standard procedures can be found, for example, in M. W. Pennington and B. N. Dunn, *Peptide Synthesis Protocols*, Humana Press, Totowa (1994). Traditional solution phase peptide synthesis can be used as well, especially when multiple protecting groups on the intermediates need to be differentiated during the deprotection and coupling reactions.

A general Fmoc-based solid phase synthesis on Rink-amide resins for Formula I is shown in Scheme 1 below. Building blocks are either commercially available or synthesized according to literature procedures known to a person skilled in the art. Coupling and deprotection conditions are chosen according to the reagents and substrates used in each reaction. The progress of each reaction is monitored by using an appropriate analytical method. The final deprotection step includes universal deprotection of protecting groups on each side chains in addition to cleavage from the Rink-amide resin to give Formula I as a C-terminal amide. Purification of the final product can be accomplished by preparative HPLC and other common purification methods.

Scheme 1

-continued

A general solution phase synthesis for Formula I is shown in Scheme 2 below. $PG^1$, $PG^4$, and $PG^5$ are appropriate protecting groups for the corresponding functional groups on reagents and intermediates. Although Scheme 2 shows specific coupling and deprotecting conditions, other conditions for the coupling steps may be used as well.

Scheme 2

A specific example Compound A may be synthesized by the synthetic procedure described in Scheme 3 below. Although specific coupling and deprotecting conditions are shown in Scheme 3, other conditions for the coupling and deprotecting steps may be used as well.

$R^5$, $R^6$ and $R^7$ are the same functional group selected from the group consisted of —C(O)OR$^{11}$, —CH$_2$OC(O)R$^{12}$. Starting from the appropriate modified peptide analog, the first step may be an esterification reaction which protects both car- Compound A Scheme 4 shows another general method to synthesize compounds of Formula I wherein $R^2$ and $R^3$ are both the same functional group selected from the group consisted of $R^{11}$, —CH$_2$OC(O)R$^{12}$, or —CH$_2$OC(O)OR$^{13}$; and wherein $R^4$, boxylic groups with the same $R^2$ moiety. The second step may be an amine protection step which protects the guanidine group on each arginine component with the same $R^4$ moiety to afford Compound B.

Scheme 4

Compound B

These detailed descriptions are presented for illustrative purposes only and are not intended as a restriction on the scope of the disclosure Proton NMR Spectra Unless otherwise indicated, all $^1$H NMR spectra were run on a Varian series Mercury 300, 400 MHz instrument or a Bruker series AV300, 400 MHz instruments. Where so characterized, all observed protons are reported as parts-per-million (ppm) downfield from tetramethylsilane (TMS) or other internal reference in the appropriate solvent indicated.

HPLC Conditions

Condition A:

Column: Boston Crest ODS, 4.6×250 mm, 5 μm

Solvent A: 0.1% trifluoroacetic acid in acetonitrile

Solvent B: 0.1% trifluoroacetic acid in water

Gradient:

| Time (min) | Solvent A (%) | Solvent B (%) |
| --- | --- | --- |
| 0.0 | 10 | 90 |
| 25.0 | 35 | 65 |
| 25.1 | 100 | 0 |
| 30.0 | Stop | |

Flow rate: 1.0 mL/min
Wavelength: 220 nm
Volume: 20 μL
Condition B:
Column: VYDAC-C18, 4.6×250 mm, 5 μm
Solvent A: 0.1% trifluoroacetic acid in acetonitrile
Solvent B: 0.1% trifluoroacetic acid in water
Gradient:

| Time (min) | Solvent A (%) | Solvent B (%) |
| --- | --- | --- |
| 0.0 | 20 | 80 |
| 25.0 | 45 | 55 |
| 25.1 | 100 | 0 |
| 30.0 | Stop | |

Flow rate: 1.0 mL/min
Wavelength: 220 nm
Volume: 5 μL
Condition C:
Column: 120A-C18, 4.6×250 mm, 5 μm
Solvent A: 0.05% trifluoroacetic acid in acetonitrile
Solvent B: 0.05% trifluoroacetic acid in water
Gradient:

| Time (min) | Solvent A (%) | Solvent B (%) |
| --- | --- | --- |
| 0.0 | 6 | 94 |
| 5.0 | 6 | 94 |
| 7.0 | 20 | 80 |
| 35.0 | 100 | 0 |
| 35.1 | Stop | |

Flow rate: 1.0 mL/min
Wavelength: 215 nm
Volume: 20 μL
Condition D:
Column: Nova-Pak C18, 3.9×150 mm
Solvent A: 0.1% trifluoroacetic acid in acetonitrile
Solvent B: 0.1% trifluoroacetic acid in water Gradient:

| Time (min) | Solvent A (%) | Solvent B (%) |
| --- | --- | --- |
| 0.0 | 10 | 90 |
| 25.0 | 35 | 65 |
| 25.1 | 100 | 0 |
| 30.0 | Stop | |

Flow rate: 1.0 mL/min
Wavelength: 220 nm
Volume: 20 μL

HEK293 Cell Assays

The Human Embryonic Kidney 293 (HEK293) cells may be cultured in suspension. After the HEK293 cells are collected, the cells may be washed 3 times with PBS buffer before the assay.

The stock solution of peptide-based compounds may be made by dissolving the compound in PBS buffers or in DMSO. Other solutions or solvents may be used to dissolve the peptide-based compounds for this assay.

Assay Procedure:

1. Mix $1.0 \times 10^6$ HEK293 cells with 100 μL PBS buffer.
2. Add 10 μL of the stock solution of the peptide-based compound prepared above so that the final concentration of the peptide-based compound is around 1/10th of that of the stock.
3. Incubate the resulting mixture at 37° C. for 3, 5, 10, 20, or 30 min.
4. Remove the cells by centrifugation.
5. Collect an aliquot of the supernatant solution (20 μL) and loaded it onto a reverse-phase HPLC column (3.9×150 Nova-Pak C18, Waters, Mass., USA) on an HPLC system (125 solvent module, System Gold, Beckman, Calif., USA). Peptide peaks may be detected at the wavelength of 220 nm (Diode Array Detector module 168, Beckman, Calif., USA).

Synthesis of Compounds

The compounds of Formula I may be synthesized according to the procedures described in the Schemes 1-4 to those skilled in the art, wherein the substituents are as defined for Formula I above, except where further noted. The synthetic methods described below are merely exemplary, and the compounds of the disclosure may also be synthesized by alternate routes as appreciated by persons of ordinary skill in the art.

Example 1

Preparation of Compound 1: Ac-Glu(OMe)-Glu(OMe)-Met-Gln-Arg-Arg-NH$_2$

Compound 1

Method A:

Step 1: Preparation of Methanolic HCl Reagent

Acetyl chloride (800 μL) was added dropwise to a stirring solution of MeOH (5.0 mL). After the addition was complete, the resulting mixture was stirred at room temperature for 5 min.

Step 2: Preparation of Ac-Glu(OMe)-Glu(OMe)-Met-Gln-Arg-Arg-NH$_2$

A solution of Compound 2, Ac-Glu-Glu-Met-Gln-Arg-Arg-NH$_2$, (90 mg) in MeOH (1.0 mL) was treated with methanolic HCl reagent (4.0 mL) made in step 1. The resulting mixture was stirred at room temperature for 2 hr, and lyophilized at room temperature to give Compound 1, Ac-Glu(OMe)-Glu(OMe)-Met-Gln-Arg-Arg-NH$_2$, (90 mg) as white amorphous solids. MS m/z 918 [M+1].

Method B:

In addition, Compound 1, Ac-Glu(OMe)-Glu(OMe)-Met-Gln-Arg-Arg-NH$_2$ was prepared according to Scheme 1. When analyzed using HPLC method A, the retention time of the desired product was about 10.2 min and its purity was about 98.8%. MS m/z 918 [M+1].

Another batch of the title compound was synthesized according to Scheme 1. When analyzed using HPLC method B, the retention time of the desired product was about 14.7 min and its purity was about 91.6%. MS m/z 918 [M+1].

Example 2

Preparation of Compound 3: Ac-Glu(OMe)-Glu(OMe)-Met-Gln-Arg(Boc)$_2$-Arg(Boc)$_2$-NH$_2$ Compound 3

Compound 3, Ac-Glu(OMe)-Glu(OMe)-Met-Gln-Arg(Boc)$_2$-Arg(Boc)$_2$-NH$_2$, (white amorphous solids) was synthesized according to Scheme 1. When analyzed by HPLC method C, the retention time of the desired product was about 28.4 min and its purity was about 97.1%. MS m/z 1319 [M+1].

Example 3

Preparation of Compound 4: Ac-Glu(OBu-t)-Glu(OBu-t)-Met-Gln-Arg(Boc)$_2$-Arg(Boc)$_2$-NH$_2$ Compound 4

Compound 4, Ac-Glu(OBu-t)-Glu(OBu-t)-Met-Gln-Arg(Boc)$_2$-Arg(Boc)$_2$-NH$_2$, (white amorphous solids) was synthesized according to Scheme 1. MS m/z 1402 [M+1].

Example 4

Preparation of Compound 5: Ac-Glu(OMe)-Glu(OMe)-Met-Gln-Arg(Ac)$_2$-Arg(Ac)$_2$-NH$_2$ Compound 5

Compound 5, Ac-Glu(OMe)-Glu(OMe)-Met-Gln-Arg(Ac)$_2$-Arg(Ac)$_2$-NH$_2$, (white amorphous solids) was synthesized from Compound 1 according to Scheme 4. The acetylation reaction was performed with Compound 1 in the presence of 5% acetic anhydride and 6% lutidine in DMF for 30 min. The crude product was purified by preparative HPLC. MS m/z 1086 [M+1].

Example 5

Preparation of Compound 6: Ac-Glu(OPr-i)-Glu(OPr-i)-Met-Gln-Arg-Arg-NH$_2$

Compound 6 was synthesized using the methods described in Example 1 after necessary changed in either the reagents or precursors used in the reactions. MS m/z 974 [M+1].

Example 6

Evaluation of Biological Degradation of Compound 2

Figure 1:
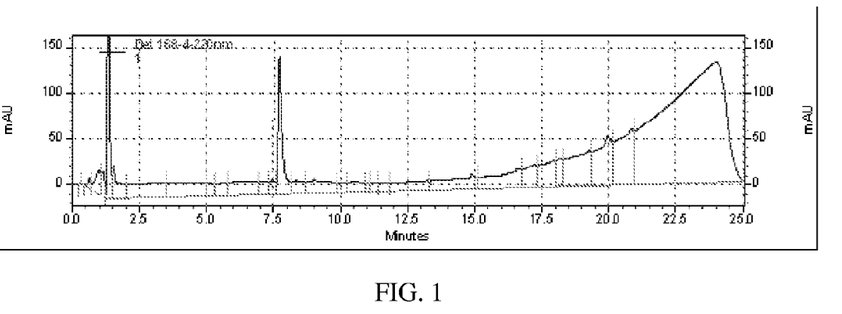
FIG. 1 depicts the HPLC results of Compound 2 in PBS buffer, under condition D as described in Example 6.

Compound 2 was used to prepare a Stock Solution 1 in PBS buffer (1 mg/mL). An aliquot of Stock Solution 1 (20 μL) was analyzed using HPLC condition D. The result was shown in FIG. 1. It appeared that Compound 1 had a retention time of about 7.7 min.

Figure 2:
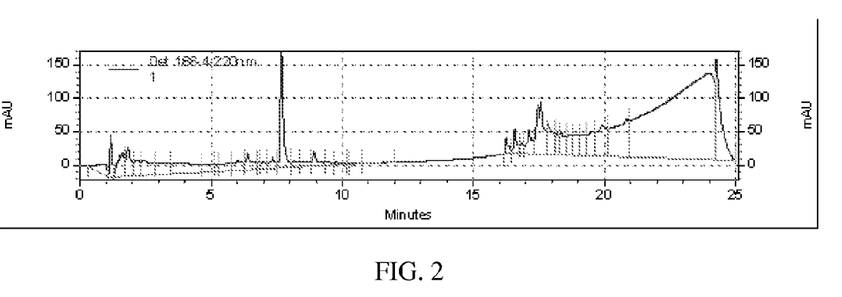
FIG. 2 depicts the HPLC results of Compound 2 after HEK293 cell assay for 10 min, under condition D as described in Example 6.
Figure 3:
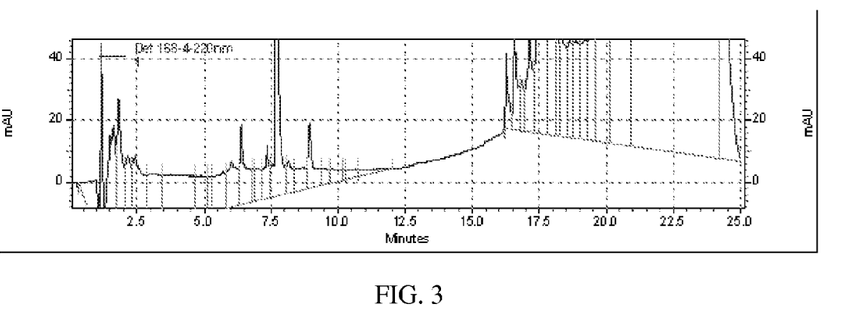
FIG. 3 is a partial enlargement of FIG. 2.

An aliquot of Stock Solution 1 (10 μL) was incubated with 1.0×10$^6$ HEK293 cells for 10 min according to the HEK293

Compound 6 cell assay procedure describe above. The results analyzed using HPLC condition D are shown in FIGS. 2-3. FIG. 3 is an enlarged version of FIG. 2.

As shown in FIGS. 2-3, Compound 2 was degraded to at least two fragments with retention time of about 6.3 min and about 8.9 min, respectively, after incubation with HEK293 cells.

Example 7

Evaluation of Biological Degradation of Compound 3

Figure 4:
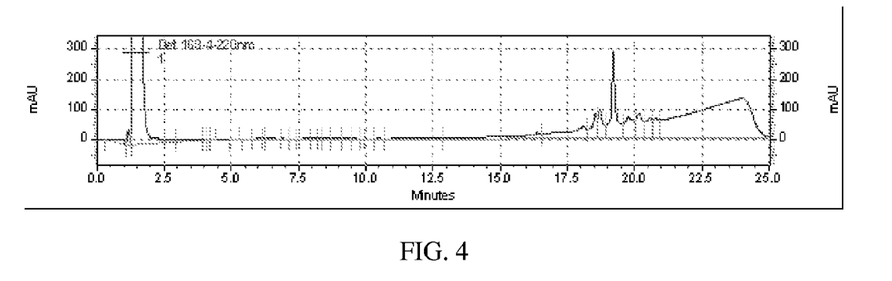
FIG. 4 depicts the HPLC results of Compound 3 after HEK293 cell assay for 5 min, under condition D as described in Example 7.
Figure 5:
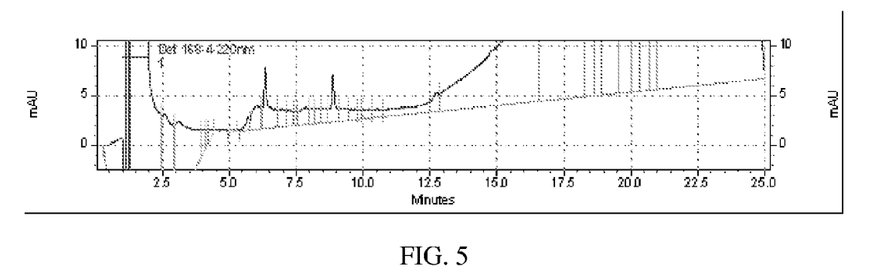
FIG. 5 is a partial enlargement of FIG. 4.

Compound 3 was used to prepare a Stock Solution 2 in DMSO (0.1 mg/mL). An aliquot of Stock Solution 2 (10 μL) was incubated with 1.0×10⁶ HEK293 cells for 5 min according to the HEK293 cell assay procedure describe above. The results analyzed using HPLC condition D are shown in FIGS. 4-5. FIG. 5 is an enlarged version of FIG. 4.

As shown in FIGS. 4-5, Compound 3 had a retention time of about 18.5 min. Compound 3 was degraded to at least two fragments with retention time of 6.3 min and 8.9 min after incubation with HEK293 cells. It appeared that the degradation profile of Compound 3 was similar to that of Compound 2. Interestingly, Compound 3 did not produce detectable intermediacy of Compound 2 in the presence of HEK293 cells. While not wishing to be bound by any theory or mechanism of action, one possible reason may be that the degradation rate of Compound 2 to fragments was faster than that of Compound 3 to Compound 2.

Figure 6:
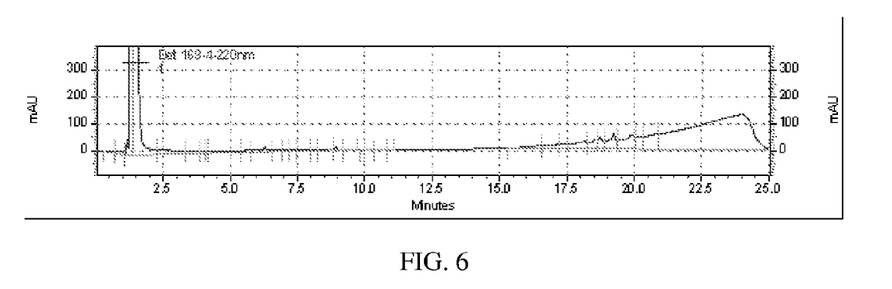
FIG. 6 depicts the HPLC results of Compound 3 after HEK293 cell assay for 10 min, under condition D as described in Example 7.
Figure 7:
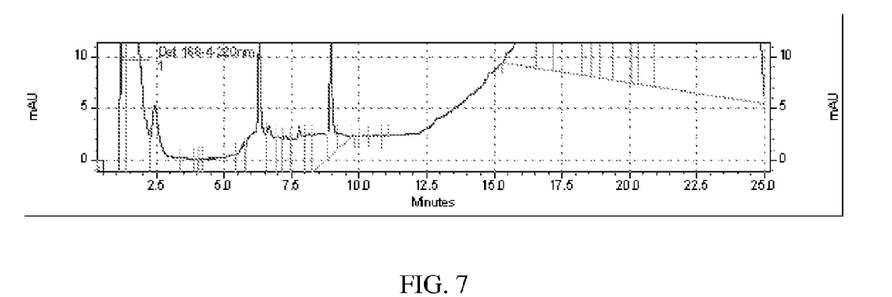
FIG. 7 is a partial enlargement of FIG. 6.

An aliquot of Stock Solution 2 (10 μL) was incubated with 1.0×10⁶ HEK293 cells for 10 min according to the HEK293 cell assay procedure describe above. The results analyzed using HPLC condition D are shown in FIGS. 6-7. FIG. 7 is an enlarged version of FIG. 6.

As shown in FIGS. 6-7, Compound 3 was completed degraded to the two fragments with retention time of 6.3 min and 8.9 min, after incubation with HEK293 cells for 10 min.

Based on the above results, it appeared that Compound 3 was degraded in the same pattern as Compound 2.

Example 8

Evaluation of Biological Degradation of Compound 1

Figure 8:
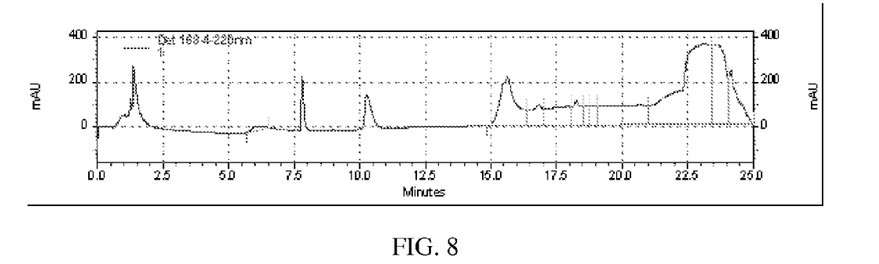
FIG. 8 depicts the HPLC results of Compounds 1 and 2 in PBS buffer, under condition D as described in Example 8.

Compound 1 was used to prepare a Stock Solution 3 in PBS buffer (1 mg/mL). An aliquot of Stock Solutions 1 (10 μL) and 3 (10 μL) was mixed and analyzed by HPLC method D. The results were shown in FIG. 8. It appeared that Compound 1 had a retention time of about 10.2 min while Compound 2 had a retention time of about 7.7 min

Figure 9:
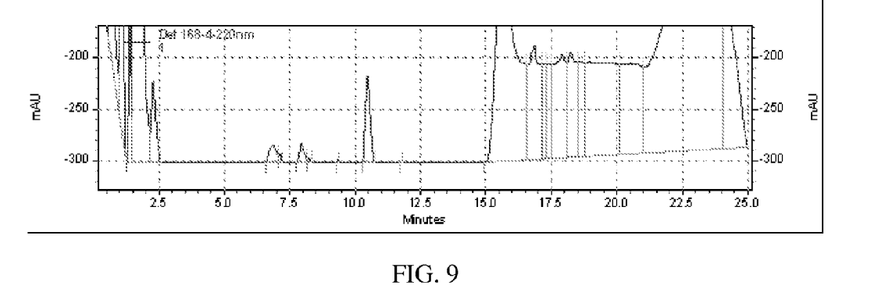
FIG. 9 depicts the HPLC results of Compound 1 and 2 after HEK293 cell assay for 3 min, under condition D as described in Example 8.

An aliquot of Stock Solution 3 (10 μL) was incubated with 1.0×10⁶ HEK293 cells for 3 min according to the HEK293 cell assay procedure describe above. The results were shown in FIG. 9. It appeared that after 3 min of incubation with HEK293 cells, Compound 1 was degraded to Compound 2 and at least one new fragment with a retention time of about 7.0 min.

Figure 10:
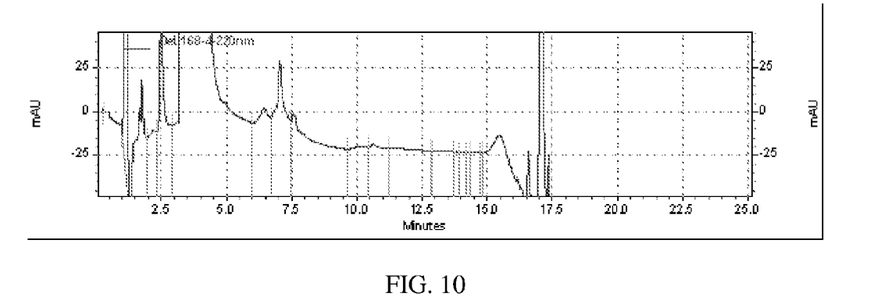
FIG. 10 depicts the HPLC results of Compound 1 and 2 after HEK293 cell assay for 30 min, under condition D as described in Example 8.

An aliquot of Stock Solution 3 (10 μL) was incubated with 1.0×10⁶ HEK293 cells for 30 min according to the HEK293 cell assay procedure describe above. The results were shown in FIG. 10. It appeared that after 30 min of incubation with HEK293 cells, Compound 1 was fully degraded to at least one new fragment. No Compound 2 was detectable after 30 min of incubation.

Compared the results of Experiments 6 and 8, it appeared that Compound 2 did not give the same degradation pattern as Compound 1.

What is claimed is:

1. A compound of Formula I:

or a pharmaceutically acceptable salt, solvate or a prodrug thereof, wherein $R^1$ is methyl;

$R^2$ and $R^3$ are independently selected from H, $R^{11}$, —$CH_2OC(O)R^{12}$, and —$CH_2OC(O)OR^{13}$;

$R^4$, $R^5$, $R^6$ and $R^7$ are independently selected from H, —$C(O)OR^{11}$, —$CH_2OC(O)R^{12}$, —$CH_2OC(O)OR^{11}$, and —$C(O)OCH_2OC(O)R^{12}$;

$R^{11}$ is $C_2$-$C_{10}$ alkyl;

$R^{12}$ is $C_1$-$C_{10}$ alkyl; and $R^{13}$ is $C_2$-$C_{10}$ alkyl;

with the proviso that at least one of $R^4$, $R^5$, $R^6$ and $R^7$ is not H.

2. The compound of claim 1, wherein $R^2$ and $R^3$ are hydrogen.

3. The compound of claim 1, wherein $R^2$ and $R^3$ are independently $C_2$-$C_{10}$ alkyl.

4. The compound of claim 1, wherein $R^4$, $R^5$, $R^6$ and $R^7$ are independently selected from the group consisting of —$C(O)OR^{11}$, —$CH_2OC(O)R^{12}$, —$CH_2OC(O)OR^{11}$, and —$C(O)OCH_2OC(O)R^{12}$.

5. The compound of claim 3, wherein at least one of $R^4$ and $R^5$ is selected from the group consisting of —$C(O)OR^{11}$, —$CH_2OC(O)R^{12}$, —$CH_2OC(O)OR^{11}$, and —$C(O)OCH_2OC(O)R^{12}$.

6. The compound of claim 3, wherein at least one of $R^6$ and $R^7$ is selected from the group consisting of —$C(O)OR^{11}$, —$CH_2OC(O)R^{12}$, —$CH_2OC(O)OR^{11}$, and —$C(O)OCH_2OC(O)R^{12}$.

7. The compound of claim 4, wherein $R^2$ and $R^3$ are hydrogen.

8. The compound of claim 4, wherein $R^2$ and $R^3$ are $R^{11}$.

9. A cosmetic composition comprising a compound of Formula I and a cosmetically acceptable adjuvant, the compound being in an amount effective for the treatment of facial wrinkles or facial asymmetry, wherein
  $R^1$ is methyl;
  $R^2$ and $R^3$ are independently selected from H, $R^{11}$, —$CH_2OC(O)R^{12}$, and —$CH_2OC(O)OR^{13}$;
  $R^4$, $R^5$, $R^6$ and $R^7$ are independently selected from H, —$C(O)OR^{11}$, —$CH_2OC(O)R^{12}$, —$CH_2OC(O)OR^{11}$, and —$C(O)OCH_2OC(O)R^{12}$;
  $R^{11}$ is $C_2$-$C_{10}$ alkyl;
  $R^{12}$ is $C_1$-$C_{10}$ alkyl; and
  $R^{13}$ is $C_2$-$C_{10}$ alkyl;
  with the proviso that at least one of $R^4$, $R^5$, $R^6$ and $R^7$ is not H.

10. The cosmetic composition according to claim 9, further comprising a safe and effective amount of at least one additional skin care active selected from the group consisting of antioxidant, anti-inflammatory, dermal matrix precursor, skin circulation promoter, vitamin, moisturizer, and skin softener, skin whitener, botanical dermal matrix builder, anti-cholinergic peptide, sunscreen, metalloproteinase inhibitor, and healing agent.

11. The cosmetic composition according to claim 9, further comprising an acceptable inert base, the acceptable inert base being selected from the group consisting of gel, lotion, cream, serum, paste, filler and transdermal patch.

12. The cosmetic composition according to claim 10, wherein the additional skin care active is an anti-oxidant and anti-inflammatory agent, the anti-oxidant and anti-inflammatory agent being selected from the group comprising lycopene and green tea extract.

13. The cosmetic composition according to claim 10, wherein the additional skin care active is a moisturizer, anti-inflammatory and healing agent, the moisturizer, anti-inflammatory and healing agent being selected from the group comprising allantoin.

14. The cosmetic composition according to claim 10, wherein the additional skin care active is hydrolyzed wheat protein.

15. The cosmetic composition according to claim 10, wherein the additional skin care active is a dermal matrix collagen precursor, the dermal matrix collagen precursor being selected from a group comprising marine collagen.

* * * * *